(12) United States Patent
Perreault

(10) Patent No.: US 9,009,922 B2
(45) Date of Patent: Apr. 21, 2015

(54) STETHOSCOPE HOLSTER

(71) Applicant: Kevin J. Perreault, Greenville, SC (US)

(72) Inventor: Kevin J. Perreault, Greenville, SC (US)

( * ) Notice: Subject to any disclaimer, the term of this patent is extended or adjusted under 35 U.S.C. 154(b) by 186 days.

(21) Appl. No.: 13/737,314

(22) Filed: Jan. 9, 2013

(65) Prior Publication Data
US 2014/0331457 A1    Nov. 13, 2014

(51) Int. Cl.
*A45F 5/02* (2006.01)
*A61B 19/00* (2006.01)
*A61B 7/00* (2006.01)

(52) U.S. Cl.
CPC ... *A45F 5/02* (2013.01); *A61B 7/00* (2013.01); *A61B 19/26* (2013.01); *A61B 2019/267* (2013.01)

(58) Field of Classification Search
USPC .......................................................... 24/3.12
See application file for complete search history.

(56) References Cited

U.S. PATENT DOCUMENTS

| | | | |
|---|---|---|---|
| 742,790 A | 10/1903 | Jones | |
| 3,878,589 A * | 4/1975 | Schaefer | 24/669 |
| 4,718,586 A | 1/1988 | Hagino | |
| 5,451,725 A | 9/1995 | Goldman | |
| 5,620,120 A * | 4/1997 | Tien | 224/199 |
| 5,692,657 A | 12/1997 | Kilo et al. | |
| 5,730,342 A | 3/1998 | Tien | |
| 5,738,432 A | 4/1998 | Okko et al. | |
| 5,799,847 A * | 9/1998 | Sandor | 224/197 |
| 5,850,954 A | 12/1998 | Dong-Joo | |
| 5,906,031 A * | 5/1999 | Jensen | 24/3.12 |
| 6,006,969 A | 12/1999 | Kim | |
| 6,065,563 A | 5/2000 | Stowers | |
| 6,283,348 B1 | 9/2001 | Wang | |
| 6,340,350 B1 * | 1/2002 | Simms | 600/528 |
| 6,419,133 B1 | 7/2002 | Grose | |
| 6,484,918 B1 | 11/2002 | Lefebvre | |
| 6,578,745 B1 * | 6/2003 | Taylor et al. | 224/197 |
| 6,736,136 B2 * | 5/2004 | Chen-Lieh | 128/201.11 |
| 7,077,302 B2 * | 7/2006 | Chuang | 224/420 |
| 7,354,304 B2 | 4/2008 | Livingston | |
| 7,458,489 B1 * | 12/2008 | Mudd et al. | 224/197 |
| 8,033,518 B2 | 10/2011 | Schuchman | |
| 8,075,202 B1 * | 12/2011 | Chamberlayne | 396/423 |
| 8,292,521 B2 * | 10/2012 | Chamberlayne | 396/423 |
| 8,708,583 B2 * | 4/2014 | Chamberlayne | 396/423 |
| 2006/0219472 A1 * | 10/2006 | Vance | 181/131 |
| 2010/0288801 A1 | 11/2010 | Messner | |
| 2011/0290841 A1 | 12/2011 | Philippe | |
| 2012/0292363 A1 | 11/2012 | Crawford | |

FOREIGN PATENT DOCUMENTS

JP    2009285021 A    12/2009

* cited by examiner

*Primary Examiner* — Robert J Sandy
*Assistant Examiner* — Louis Mercado
(74) *Attorney, Agent, or Firm* — Amy Allen Hinson; Nexsen Pruet, LLC

(57) ABSTRACT

A reversibly locking assembly for use as a stethoscope holster or for use with other devices. The assembly includes a clip adapted for attachment to an article of clothing wherein the clip has a clip channel wherein the clip channel includes an upper section and a lower section wherein the lower section is wider than the upper section. A stethoscope connector is provided which is adapted for attachment to a stethoscope. The stethoscope has a tube and when the tube is aligned with the clip channel the asymmetric plate passes through the upper section. When the tube is not aligned with the clip channel the asymmetric plate does not pass through the upper section.

17 Claims, 6 Drawing Sheets

STETHOSCOPE HOLSTER

BACKGROUND

The present invention is related to a holster, and more specifically, a holster for holding a stethoscope, or other device, wherein the stethoscope or device rotates a connector to secure the stethoscope or device when stored but it is easily retrieved when needed.

Stethoscopes are widely used throughout the medical industry. It is often the case that a stethoscope is needed in an emergency situation and those situations are not always predictable. There has been a myriad of techniques and devices throughout the generations for holding a stethoscope yet all of them are inferior for one reason or another resulting in most users simply wearing them around their neck which is not a suitable solution. Other devices suffer from the, same deficiency.

There has been a long standing need for a stethoscope holster which is easily stored and retrieved without delay. Such a device is provided herein.

SUMMARY

It is an object of the invention to provide a stethoscope holster which maintains the stethoscope in a convenient location for easy retrieval.

It is another object of the invention to provide a stethoscope holder wherein the stethoscope cannot be easily dislodged from the holster during routine activity yet it can be easily removed for intended use.

These and other embodiments, as will be realized, are provided in a stethoscope holster. The stethoscope holder comprises a clip adapted for attachment to an article of clothing wherein the clip comprises a clip channel wherein the clip channel comprises an upper section and a lower section wherein the lower section is wider than the upper section. A stethoscope connector is provided which is adapted for attachment to a stethoscope. The stethoscope has a tube and when the tube is aligned with the clip channel the assymettric plate passes through the upper section. When the tube is not aligned with the clip channel the assymetric plate does not pass through the upper section.

Yet another embodiment is provided in a reversibly locking assembly. The reversibly locking assembly has a clip adapted for attachment to an article of clothing wherein the clip comprises a clip channel. The clip channel comprises an upper section and a lower section wherein the lower section is wider than the upper section. A connector wherein the connector comprises an assymetric plate which passes through the upper section in a first rotational orientation and does not pass through the upper section in a second rotational orientation. A device is attached to the connector wherein the device is assymetrically weighted such that when the assymetric plate is in the clip channel the assymetrically weighted device rotates the assymetric plate to the second rotational orientation

DESCRIPTION

The present invention is related to a stethoscope holster for securely and conveniently holding a stethoscope or other device close to the body yet the stethoscope or other device can be easily and rapidly retrieved for use.

The invention will be described with reference to the figures which are an integral non-limiting component of the invention. Throughout the description similar elements will be numbered accordingly.

Figure 1:
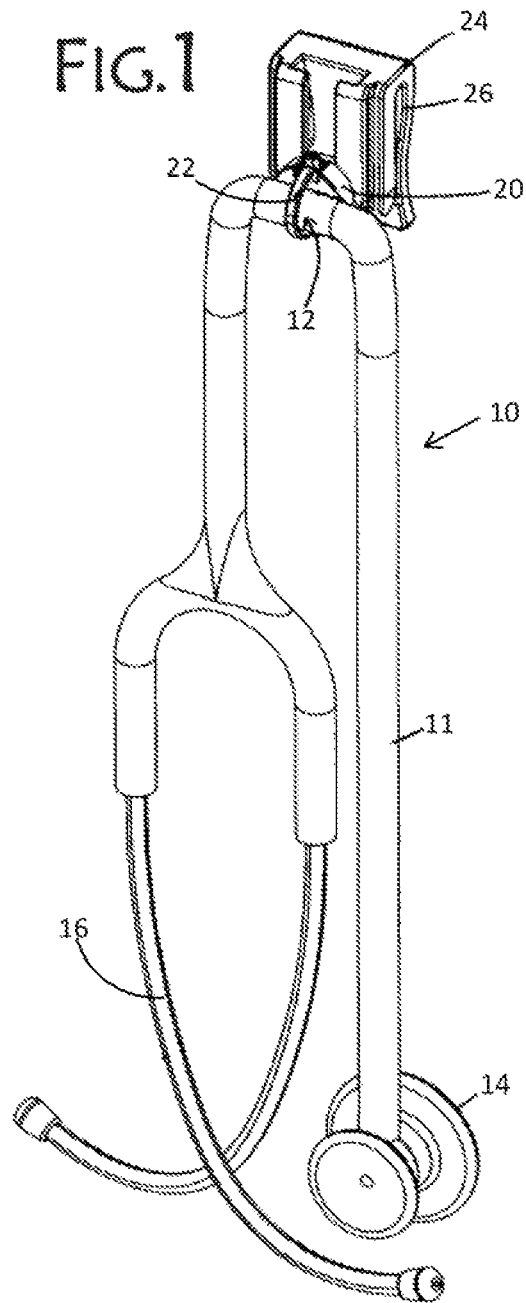
FIG. 1 is a perspective view of an embodiment of the invention.

An embodiment of the invention is illustrated in FIG. 1. In FIG. 1, a stethoscope is generally represented at 10. The stethoscope comprises a bell, 14, which captures sound from the patient wherein the sound is transmitted through tubing, 11, to ear pieces, 16, thereby allowing the medical professional to have a clear sound of the body sounds of interest. A stethoscope connector, 20, is attached to the stethoscope, preferably along the tube, at a connection point, 12. In one embodiment of the invention the connection point is at a point wherein the weight of those portions of the stethoscope to one side of the connection point is higher than the weight of those portions of the stethoscope to the other side of the connection point. In one embodiment the weight of the components on the bell side of the stethoscope is higher than the weight of the stethoscope components on the ear piece side of the connection point. The reason for the assymettric weight distribution will be more readily understood upon further discussion. Though not limited thereto, the stethoscope may be attached to the stethoscope connector by a strap, 22, wherein the strap and stethoscope connector at least partially circumnavigate the tube without constricting the tube. The manner in which the stethoscope is attached to the stethoscope connector is selected to meet the criteria of not allowing the tube to slide therein parallel to the tube and which does not constrict the tube to an amount sufficient to restrict sound from transmitting thereby within the tube. The stethoscope connector is received by a clip, 24, which may be adapted for securing to a belt such as by friction fit or secured to an article of clothing. A slot, 26, for friction fit over a belt is particularly suitable for demonstration of the invention due to the simplicity of use and convenience in manufacture.

Figure 2:
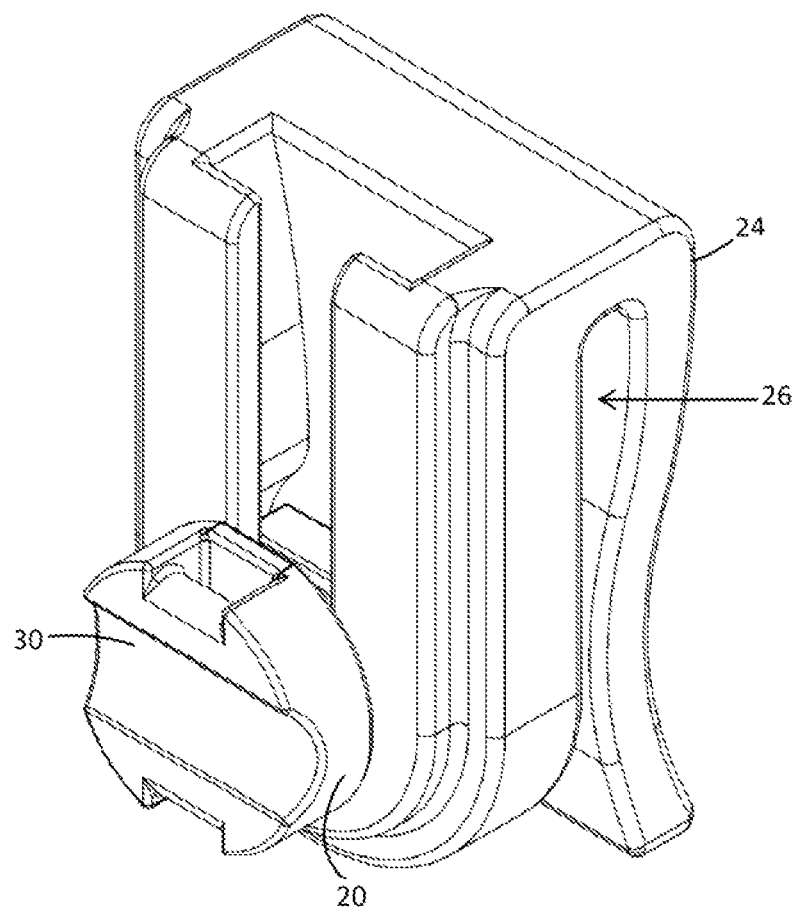
FIG. 2 is a perspective view of the embodiment of FIG. 1 without the stethoscope.
Figure 3:
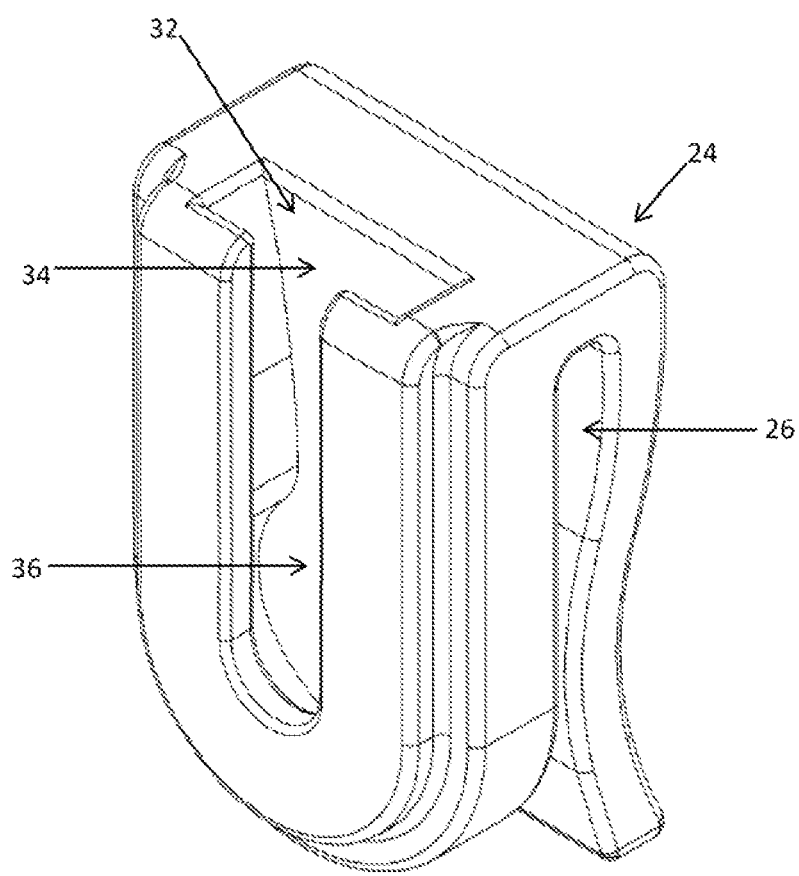
FIG. 3 is a perspective view of a clip of the invention.
Figure 4:
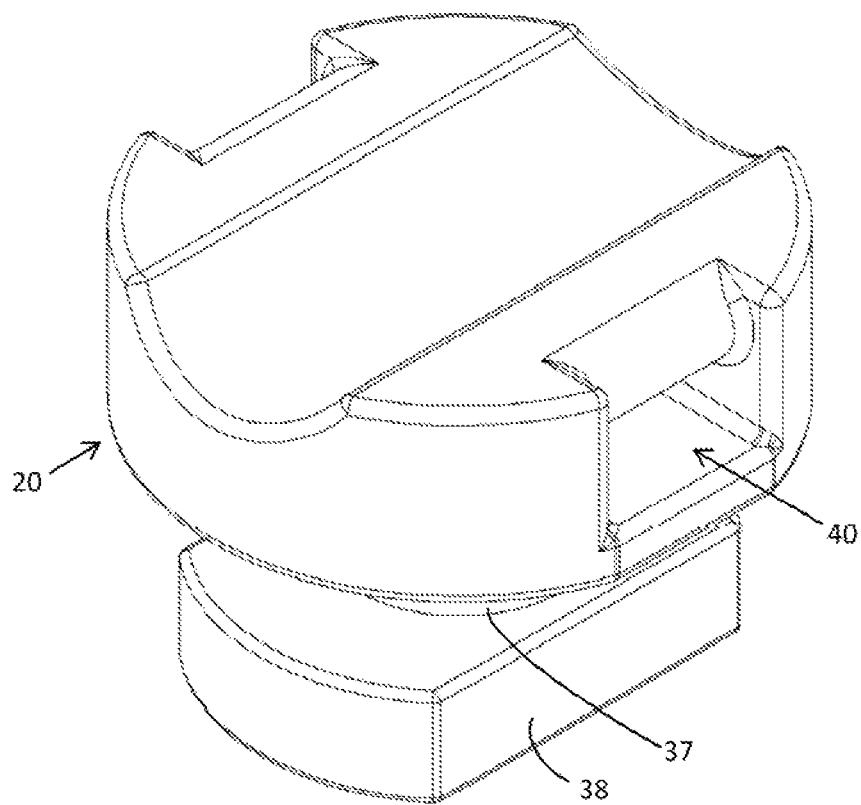
FIG. 4 is a perspective view of a stethoscope connector of the invention.

A schematic view of the stethoscope connector, 20, and clip, 24, is provided in FIG. 2 wherein the stethoscope is removed for clarity. An isolated view of the clip is provided in FIG. 3 and an isolated view of the stethoscope connector is provided in FIG. 4. An optional but preferred stethoscope channel, 30, is provided in the stethoscope connector, 20, for convenience in locating the stethoscope during assembly. For the purposes of discussion, the stethoscope channel will be used to represent the orientation of the tube at the stethoscope connector with the understanding that this is for clarity in discussion and not a limitation since the stethoscope channel is optional. The configuration illustrated in FIG. 2 represents the relationship between the stethoscope connector and clip during storage. As illustrated in FIG. 3, the clip comprises a clip channel, 32, with an upper section, 34, which is preferably substantially rectangular or trapezoidal and a lower section, 36, which is wider than the upper section. The lower section is preferably arcuate. The stethoscope connector, 20, comprises a rear pedestal, 37, with an asymmetrical plate, 38, thereon. The asymmetrical plate has a narrow portion and a wider portion wherein the narrow portion will pass through the upper section yet if rotated the wider portion will not pass through the narrow portion. The stethoscope orientation, as represented by the stethoscope channel for the purposes of discussion, is such that the narrow portion is aligned with the upper section for passage therethrough. Upon releasing the stethoscope the asymmetrical weight causes the stethoscope connector to rotate thereby changing the orientation of the narrow portion and wider portion such that the asymmetrical plate cannot transit through the narrow portion without rotational manipulation, A strap channel, 40, receives the strap which is discussed above.

With reference back to FIG. 1, the stethoscope is in the storage position wherein the stethoscope connector is prohibited from transiting through the upper section. If either end of the stethoscope is lifted and pulled upward, the weight of the opposite end will persuade the stethoscope connector to rotate thereby orienting the stethoscope connector such that the asymmetrical plate can transit the narrow portion of the clip channel. When returned, the stethoscope is grasped by either end and the stethoscope will naturally rotate such that the asymmetrical plate is aligned for transit through the narrow upper portion. As the stethoscope is released from the hand, the gravitational forces will persuade the stethoscope holder to rotate such that the asymmetrical plate will not transit the narrow portion.

Figure 5:
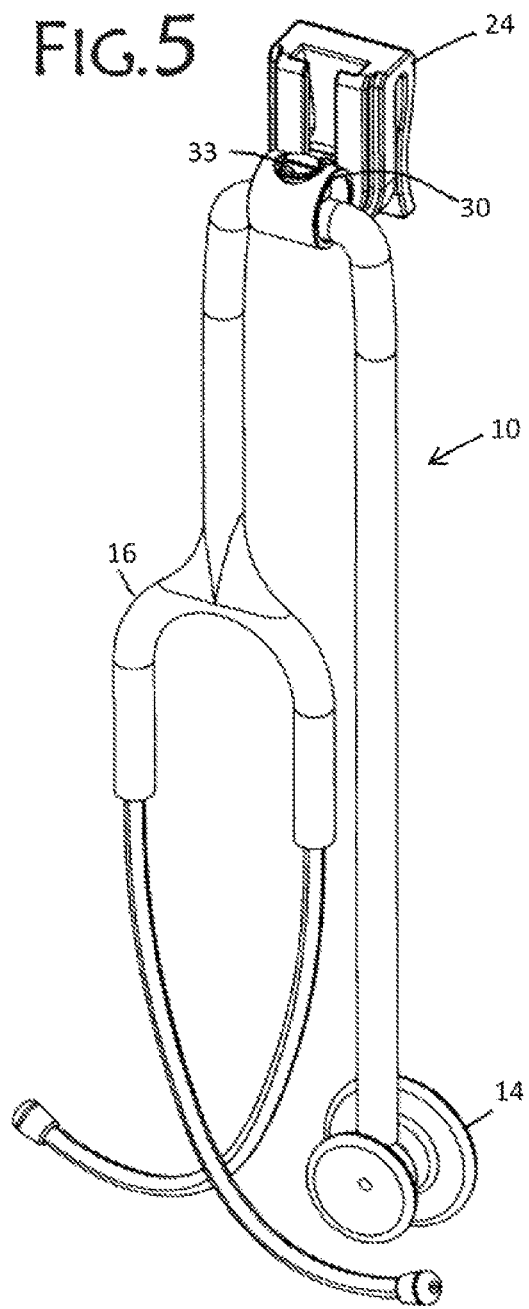
FIG. 5 is a perspective view of an embodiment of the invention.
Figure 6:
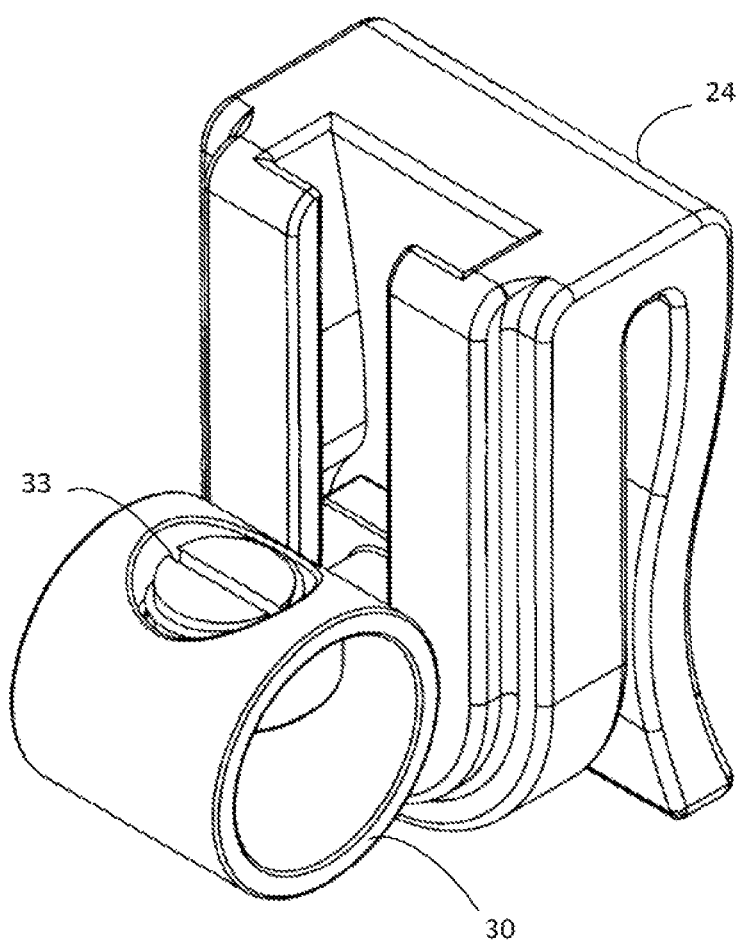
FIG. 6 is a perspective view of the embodiment of FIG. 5 without the stethoscope.

An embodiment of the invention is illustrated in FIG. 5 wherein the stethoscope and clip are as defined above. A set screw stethoscope connector, 30, is illustrated wherein the tube is received by a collar and secured therein by a set screw, 33, which is rotationally attached to the collar and engages with the tube to secure the tube in position by friction. An embodiment of the clip and set screw stethoscope connector is illustrated in Fig, 6 wherein the stethoscope is removed to facilitate visualizing the set screw stethoscope connector.

Though illustrated with a stethoscope the connector and clip may be employed with a myriad of device, medical or otherwise, wherein it is desirous to have the device in close proximity to the body and yet readily available. Though not limited thereto drink or food containers and emergency equipment are listed as exemplary devices.

The invention has been described with reference to the preferred embodiments without limit thereto. One of skill in the art would realize additional embodiments and alternations which even though not enumerated are within the scope of the invention as more specifically set forth in the claims appended hereto.

The invention claimed is:

1. A stethoscope holster comprising:
   a clip adapted for attachment to an article of clothing wherein said clip comprises a clip channel wherein said clip channel comprises with an upper section and a lower section wherein said lower section is wider than said upper section; and
   a stethoscope connector comprises an asymmetric plate, the stethoscope connector adapted for attachment to a stethoscope wherein said stethoscope has a tube and when said tube is aligned with said clip channel at said stethoscope connector said asymmetric plate passes through said upper section and when said tube is not aligned with said clip channel said asymmetric plate does not pass through said upper section;
   wherein said stethoscope connector comprises a collar for receiving said tube.

2. The stethoscope holster of claim 1 further comprising a set screw rotationally engaged with said collar wherein said set screw is rotationally engaged with said tube.

3. The stethoscope holster of claim 1 further comprising a pedestal between said asymmetric plate and said attachment to said stethoscope.

4. The stethoscope holster of claim 1 wherein said asymmetric plate comprises semi-circular faces.

5. The stethoscope holster of claim 1 wherein said lower section comprises arcuate regions.

6. The stethoscope holster of claim 1 wherein said stethoscope connector comprises a stethoscope channel.

7. The stethoscope holster of claim 1 wherein said stethoscope connector attaches to said tube with said stethoscope asymmetrically weighted relative to a connection point of said stethoscope.

8. A reversibly locking assembly comprising:
   a clip adapted for attachment to an article of clothing wherein said clip comprises a clip channel wherein said clip channel comprises an upper section and a lower section wherein said lower section is wider than said upper section;
   a connector wherein said connector comprises a collar for receiving a tube and an asymmetric plate which passes through said upper section in a first rotational orientation and does not pass through said upper section in a second rotational orientation; and
   a device attached to said connector wherein said device is asymmetrically weighted such that when said asymmetric plate is in said clip channel said asymmetrically weighted device rotates said asymmetric plate to said second rotational orientation.

9. The reversibly locking assembly of claim 8 wherein said device is a stethoscope.

10. The reversibly locking assembly of claim 8 further comprising a set screw rotationally engaged with said collar wherein said set screw is rotationally engaged with said device.

11. The reversibly locking assembly of claim 8 further comprising a pedestal between said asymmetric plate and said connector.

12. The reversibly locking assembly of claim 8 wherein said asymmetric plate comprises semi-circular faces.

13. The reversibly locking assembly of claim 8 wherein said lower section comprises arcuate regions.

14. A reversibly locking assembly comprising:
   a clip adapted for attachment to an article of clothing wherein said clip comprises a clip channel wherein said clip channel comprises an upper section and a lower section wherein said lower section is wider than said upper section;
   a connector wherein said connector comprises a asymmetric plate which passes through said upper section in a first rotational orientation and does not pass through said upper section in a second rotational orientation; and
   a device attached to said connector wherein said device is a stethoscope and is asymmetrically weighted such that when said asymmetric plate is in said clip channel said asymmetrically weighted device rotated said asymmetric plate to said second rotation orientation.

15. The reversibly locking assembly of claim 14, further comprising a pedestal between said asymmetric plate and sad connector.

16. The reversibly locking assembly of claim 14 wherein said asymmetric plate comprises semi-circular faces.

17. The reversibly locking assembly of claim 14 wherein said lower section comprises arcuate regions.

* * * * *